(12) United States Patent
Schatz

(10) Patent No.: US 7,803,136 B2
(45) Date of Patent: Sep. 28, 2010

(54) MYOCARDIAL INJECTOR

(76) Inventor: Richard A. Schatz, P.O. Box 8517, Rancho Santa Fe, CA (US) 92067

( * ) Notice: Subject to any disclaimer, the term of this patent is extended or adjusted under 35 U.S.C. 154(b) by 213 days.

(21) Appl. No.: 11/422,307

(22) Filed: Jun. 5, 2006

(65) Prior Publication Data
US 2007/0282267 A1     Dec. 6, 2007

(51) Int. Cl.
*A61M 5/178*     (2006.01)
(52) U.S. Cl. .......... 604/164.03; 604/104; 604/117; 604/164.01; 604/264
(58) Field of Classification Search ......... 604/104–107, 604/117, 164.01, 164.03, 164.04, 164.08, 604/164.1, 264, 268, 272
See application file for complete search history.

(56) References Cited

U.S. PATENT DOCUMENTS

| | | | |
|---|---|---|---|
| 4,582,181 A | 4/1986 | Samson | |
| 4,696,667 A | 9/1987 | Masch | |
| 4,947,854 A | 8/1990 | Rabinovitz et al. | |
| 5,312,341 A | 5/1994 | Turi | |
| 5,507,795 A | 4/1996 | Chiang et al. | |
| 6,165,188 A | 12/2000 | Saadat et al. | |
| 6,582,400 B1 | 6/2003 | Hawk et al. | |
| 6,623,448 B2 * | 9/2003 | Slater | 604/95.01 |
| 6,767,338 B2 | 7/2004 | Hawk et al. | |
| 6,780,175 B1 * | 8/2004 | Sachdeva et al. | 604/531 |

* cited by examiner

*Primary Examiner*—Kevin C Sirmons
*Assistant Examiner*—Bhisma Metha
(74) *Attorney, Agent, or Firm*—Nydegger & Associates

(57) ABSTRACT

A device is provided for performing intra myocardial injections. The device comprises a needle, a catheter formed with a lumen, and an abutment member mounted within the lumen for axial movement. The abutment member is movable between a first configuration, wherein it is substantially tube-like and is positioned within the lumen of the catheter, and a second configuration, wherein it extends beyond the distal end of the catheter and is substantially radially flared. Before the needle is advanced to perform an injection, the abutment member is moved to its second configuration to prevent contact between the catheter and the myocardial tissue during the injection.

12 Claims, 2 Drawing Sheets

MYOCARDIAL INJECTOR

FIELD OF THE INVENTION

The present invention pertains generally to devices and methods for delivering medicaments to a patient. More specifically, the present invention pertains to devices and methods for performing intra myocardial injections. The present invention is particularly, but not exclusively, useful as a device and method for advancing a needle from a catheter to perform an intra myocardial injection while protecting the myocardial tissue from contact with the catheter.

BACKGROUND OF THE INVENTION

Intravascular catheters are used in a wide variety of medical procedures by inserting the catheter into the vascular system of the patient at an easily accessible location. Thereafter, the tip of the catheter is advanced through the vasculature to a desired target site. In this manner, virtually any target site in the patient's vascular system may be remotely accessed. Of particular interest here are those medical procedures that require the use of injection catheters to inject therapeutic or diagnostic agents into various target tissues within the human body. When so used, an advantage of injection catheters is that the target tissue may be accessed by minimally invasive surgical techniques.

In many applications the target tissue is within a wall of an organ, such as the heart. For instance, therapeutic or diagnostic agents such as genes, proteins, or drugs may be injected directly into the heart. When the target tissue is within the wall of an organ, however, it is often desirable to inject the therapeutic or diagnostic agent into the tissue proximate the center of the organ wall. In these applications, if the needle of the injection catheter inadvertently passes through the wall, the therapeutic or diagnostic agents that are dispensed from the distal end of the needle will not be effectively delivered to the target tissue. Further, because the injection procedure often requires the thrust of a needle in the distal direction, the required motion can cause the catheter itself to contact and perforate or otherwise injure the wall of the organ.

In light of the above, it is an object of the present invention to provide a device and method that protects the myocardial wall from injury and perforation during an intra myocardial injection. Another object of the invention is to provide a device and method for controlling the depth of an intra myocardial injection. Still another object of the invention is to provide a device and method for performing an intra myocardial injection from a catheter in which a removable barrier prevents contact between the catheter and the myocardial tissue and allows the physician to advance the needle with confidence and without fear of perforating the myocardial tissue with the catheter. Yet another object of the present invention is to provide a device and method for performing intra myocardial injections which is easy to implement, simple to perform, and cost effective.

SUMMARY OF THE INVENTION

In accordance with the present invention, an injector is provided to perform intra myocardial injections while preventing unnecessary trauma to the myocardial tissue. Structurally, the injector includes a catheter having a proximal end and a distal end. Further, the catheter is formed with a lumen that extends from the proximal end to the distal end and defines a longitudinal axis. The injector also includes a needle that is mounted within the lumen of the catheter for axial movement therein.

The injector of the present invention also includes an abutment member that has a proximal portion and a distal portion. This abutment member is mounted within the catheter for relative axial movement and is, preferably, made of wire loops formed from a nickel-titanium or other similar alloy. For purposes of the present invention, the distal portion of the abutment member is biased to flare radially outward when not contained inside the catheter. Also, the injector includes a rod having a proximal end and a distal end, with the rod mounted for axial movement within the lumen of the catheter. Importantly, the distal end of the rod is engaged with the proximal portion of the abutment member to move the abutment member within the catheter lumen.

For the operation of the present invention, the abutment member is movable by the rod between a first configuration and a second configuration. In its first configuration, the abutment member is substantially tube-like and is positioned within the lumen of the catheter. The rod moves the abutment member axially following the longitudinal axis of the lumen when moving the abutment member into its second configuration. In its second configuration, the distal portion of the abutment member extends axially beyond the distal end of the catheter and is substantially radially flared.

In order to perform an intra myocardial injection, the injector is placed at a desired position near or adjacent myocardial tissue. During this placement, the abutment member is in its first configuration. Thereafter, the rod is used to move the abutment member in the distal direction through the distal end of the catheter until the abutment member reaches its second configuration. In its second configuration, the distal portion of the abutment member flares radially and the abutment member is substantially fan shaped. Because the abutment member extends distally from the catheter, the abutment member provides a barrier between the catheter and the myocardial tissue. Therefore, when the needle is advanced and the needle tip penetrates the myocardial tissue to perform the injection, the abutment member prevents contact between the catheter and the myocardial tissue, preventing unwanted advancement of the catheter. As a result, the surgeon may confidently advance the needle without risk of damaging the myocardial tissue with the catheter.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
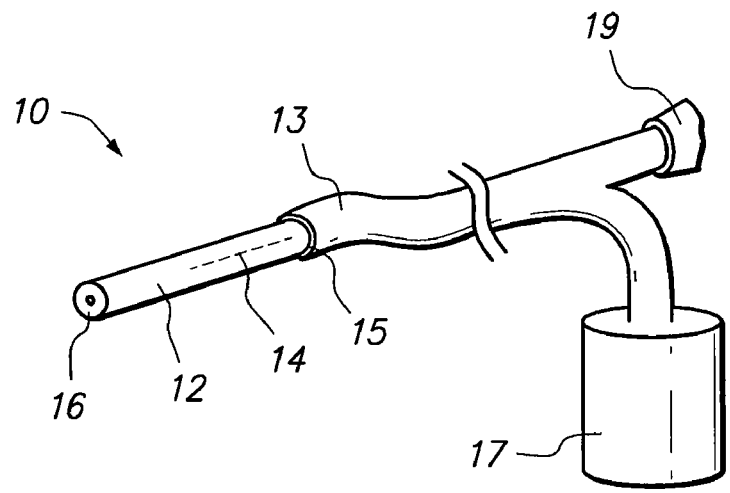
FIG. 1 is a perspective view of the intra myocardial injector in accordance with the present invention.

Referring initially to FIG. 1, an intra myocardial injector in accordance with the present invention is shown, and is generally designated 10. As shown in FIG. 1, the injector 10 includes a catheter 12 that extends along an axis 14 from a proximal end 15 to a distal end 16. As is shown, the proximal end 15 of the catheter 12 is connected to tubing 13. For purposes of the present invention, the tubing 13 is in fluid communication with a vessel 17 for holding medicament or other fluid for medical treatment. As is further shown, the tubing 13 also includes a port 19 that provides access for manipulation of internal components of the catheter 12.

Figure 2:
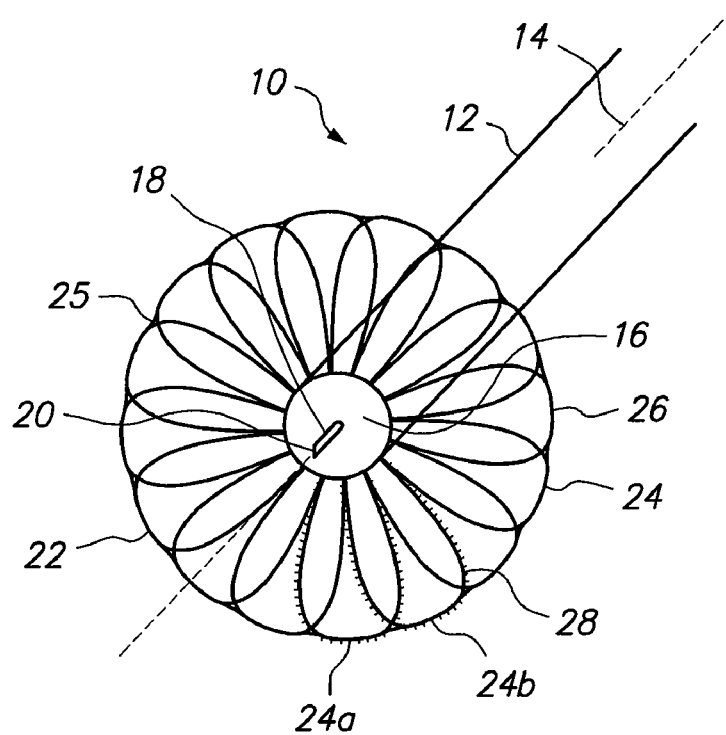
FIG. 2 is a perspective view of the intra myocardial injector of FIG. 1 shown with the abutment member in its second configuration in accordance with the present invention.

Referring now to FIG. 2, the injector 10 is shown to include a needle 18 that terminates at a needle tip 20. As shown in FIG. 2, the needle 18 has been advanced so that the needle tip 20 extends beyond the distal end 16 of the catheter 12. Further, the injector 10 is shown to include an abutment member 22. As shown, the abutment member 22 is formed from a plurality of loops 24 of wire 26. Specifically, the abutment member 22 is formed with overlapping loops 24 that are biased to radially extend from the axis 14. Further, the abutment member 22 may include a webbing 25 that interconnects adjacent loops 24. Such a webbing 25 can comprise a high-friction material. For the present invention, the abutment member 22 may include engagement elements 28 such as tines that extend from exemplary loops 24a, 24b, or a high friction surface.

Figure 3A:
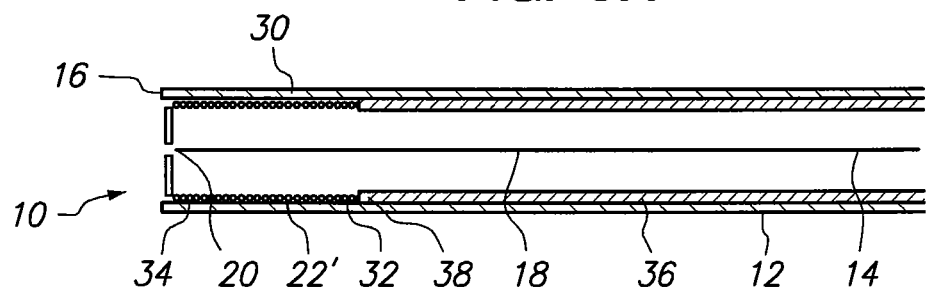
FIG. 3A is a cross sectional view of the injector of FIG. 2 shown with the abutment member in its first configuration in accordance with the present invention.

Turning now to FIG. 3A, the internal features of the injector 10 may be understood. As shown in FIG. 3A, the catheter 12 forms a lumen 30 that extends along the axis 14 to the distal end 16. Unlike in FIG. 2, the abutment member 22' is positioned completely within the lumen 30, i.e., in its first configuration. As shown, when in its first configuration, the abutment member 22' is substantially tube-like. Specifically, the abutment member 22' includes a proximal portion 32 and a distal portion 34 that are substantially cylindrical.

In FIG. 3A, it is further shown that the injector 10 includes a pusher rod 36 that includes a distal end 38. As shown, the pusher rod 36 is received within the lumen 30 and is axially movable with respect to the catheter 12. For purposes of the present invention, the distal end 38 of the pusher rod 36 engages the proximal portion 32 of the abutment member 22' to cause movement of the abutment member 22'. In certain embodiments, the rod 36 and the abutment member 22 may be a single piece.

Still referring to FIG. 3A, the needle 18 is shown positioned entirely within the lumen 30, with the end 16 of the catheter 12 distal of the needle tip 20. Structurally, the needle 18 may be mounted to a needle hub (not shown) for movement with respect to the lumen 30 of the catheter 12.

Figure 3B:
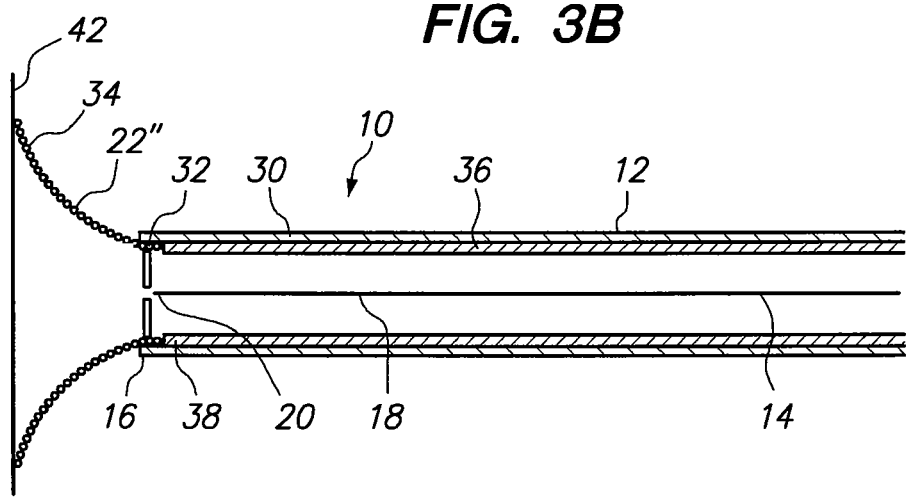
FIG. 3B is a cross sectional view of the injector of FIG. 2 shown with the abutment member in its second configuration in accordance with the present invention.

Referring now to FIG. 3B, the abutment member 22" is shown in its second configuration. Specifically, as shown, the distal portion 34 of the abutment member 22" is shown extended from the distal end 16 of the catheter 12. Because it is radially biased, the distal portion 34 of the abutment member 22" flares radially when extended beyond the distal end 16 of the catheter 12 and takes a fan shape. Stated differently, the distal portion of the abutment member 22 is flared radially outward to establish an annular-shaped barrier at the distal extreme of the abutment member 22. As shown in FIG. 3B, the needle 18 is still retracted within the catheter 12.

Figure 3C:
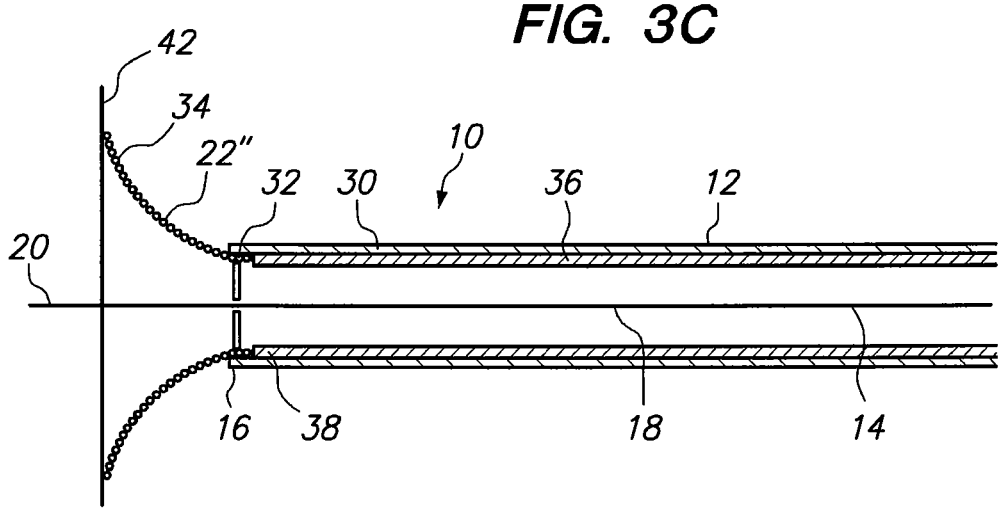
FIG. 3C is a cross sectional view of the injector of FIG. 2 shown with the abutment member in its second configuration and with the needle advanced and penetrating myocardial tissue in accordance with the present invention.

Referring now to FIG. 3C, it can be seen that the needle 18 has been advanced to extend the needle tip 20 beyond the distal end 16 of the catheter 12 and the abutment member 22". Preferably, the needle tip 20 extends between 3 and 7 millimeters beyond the distal portion 34 of the abutment member 22".

Referring now to FIGS. 3A-3C collectively, the operation of the present invention may be understood. Initially, the injector 10 is configured as in FIG. 3A with the abutment member 22' in its first configuration. When an intra myocardial injection is desired, the injector 10 is placed adjacent myocardial tissue 42. Next, as shown in FIG. 3B, the pusher rod 36 is advanced and the distal end 38 of the rod 36 forces the abutment member 22 in the distal direction. The abutment member 22 is moved distally until it reaches its second configuration. In the second configuration, the distal portion 34 of the abutment member 22" flares radially and provides a barrier between the distal end 16 of the catheter 12 and the myocardial tissue 42. When the injector 10 is moved toward the myocardial tissue 42, the abutment member 22 abuts the tissue 42 and prevents further movement of the catheter 12 in the distal direction. In further detail, FIGS. 3A and 3B show the proximal portion of the abutment member 32 inside the lumen 30 of the catheter 12 when the distal portion of the abutment member 34 is in its first configuration. As shown in FIG. 3C, the proximal portion of the abutment member 32 remains inside the lumen 30 of the catheter 12 when the distal portion of the abutment member 34 is in its second configuration. Further, the engagement elements 28 (shown in FIG. 2) on the abutment member 22 may pierce or contact and engage the myocardial tissue 42 to anchor the injector 10 in position.

With the abutment member 22" in its second configuration, the needle 18 may be linearly advanced to extend the needle tip 20 as shown in FIG. 3C. A linear advancement of the needle 18 may be accomplished by pushing the needle hub (not shown) relative to the catheter 12, or otherwise pushing the needle 18 relative to the catheter 12 as known in the art. As a result of its advancement, the needle tip 20 extends beyond the distal end 16 of the catheter 12 and beyond the distal portion 34 of the abutment member 22" to penetrate the myocardial tissue 42 to an approximate depth of between 3 and 7 millimeters. When the myocardial tissue 42 has been penetrated by the needle tip 20 at the appropriate depth, a medicament or other treatment fluid may be injected through the needle tip 20 as is well known in the art.

After the injection has been performed, the needle 18 is retracted within the lumen 30, as illustrated in FIG. 3B. Then the abutment member 22" is withdrawn into the lumen 30 by the pusher rod 36, as illustrated in FIG. 3A. Thereafter, the injector 10 is removed from the patient's vasculature.

While the particular Myocardial Injector as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An intra myocardial injector which comprises:
a catheter having a distal end, said catheter being formed with a lumen defining a longitudinal axis;
an abutment member having a distal portion and a proximal portion, wherein the abutment member is movable between a first configuration and a second configuration wherein in its first configuration the abutment member is substantially tube-shaped and is positioned within the lumen of the catheter and in its second configuration the proximal portion remains in the lumen of the catheter while the distal portion of the abutment member extends axially beyond the distal end of the catheter and is flared radially outward to establish an annular-shaped barrier at a distal extreme of the abutment member;

a pusher rod for axially moving the abutment member between the first configuration and the second configuration; and a needle having a tip, said needle being positioned within the lumen of the catheter for a linear advancement of the needle tip beyond the distal end of the catheter and beyond the barrier provided by the distal portion of the abutment member to penetrate myocardial tissue to perform an injection, when said abutment member is in its second configuration and the annular-shaped barrier abuts the myocardial tissue to prevent contact between said catheter and the myocardial tissue and prevent further distal movement of the catheter during the infection.

2. An injector as recited in claim 1 wherein the abutment member is comprised of wire formed from a nickel-titanium alloy.

3. An injector as recited in claim 2 wherein the abutment member is formed from loops of the nickel-titanium wire.

4. An injector as recited in claim 3 wherein the abutment member includes engagement elements on the loops of the wire.

5. An injector as recited in claim 3 wherein a webbing interconnects the loops of the nickel-titanium wire.

6. An injector as recited in claim 1 wherein the pusher rod engages the proximal portion of the abutment member to axially move the abutment member between the first configuration and the second configuration.

7. An intra myocardial injector which comprises:

a catheter having a distal end, said catheter being formed with a lumen defining a longitudinal axis;

an abutment member having a distal portion and a proximal portion, movable between a first configuration and a second configuration wherein in its first configuration the abutment member is substantially tube-shaped and is positioned within the lumen of the catheter and in its second configuration the proximal portion remains in the lumen of the catheter while the distal portion of the abutment member extends axially beyond the distal end of the catheter and is flared radially outward to establish an annular-shaped barrier a distal extreme of the abutment member;

a pusher rod having a distal end, with said pusher rod being mounted within the lumen of the catheter for axial movement therein, and with said distal end of the pusher rod engaging the proximal portion of the abutment member to move the abutment member between the first configuration and the second configuration; and a needle having a tip, said needle being positioned within the lumen of the catheter for a linear advancement of the needle tip beyond the distal end of the catheter and beyond the barrier provided by the distal portion of the abutment member to penetrate myocardial tissue to perform an injection, when said abutment member is in its second configuration and the annular-shaped barrier abuts the myocardial tissue to prevent contact between said catheter and the myocardial tissue and prevent further distal movement of the catheter during the injection.

8. An injector as recited in claim 7 wherein the abutment member is comprised of wire formed from a nickel-titanium alloy.

9. An injector as recited in claim 8 wherein the abutment member is formed from loops of the nickel-titanium wire.

10. An injector as recited in claim 9 wherein the abutment member includes engagement members on the loops of wire.

11. An injector as recited in claim 9 wherein a webbing interconnects the loops of the nickel-titanium wire.

12. An injector as recited in claim 7 wherein the pusher rod engages the proximal portion of the abutment member to axially move the abutment member between the first configuration and the second configuration.

* * * * *

UNITED STATES PATENT AND TRADEMARK OFFICE
CERTIFICATE OF CORRECTION

PATENT NO. : 7,803,136 B2  Page 1 of 1
APPLICATION NO. : 11/422307
DATED : September 28, 2010
INVENTOR(S) : Richard A. Schatz It is certified that error appears in the above-identified patent and that said Letters Patent is hereby corrected as shown below:

Column 3, Line 64:
DELETE "22"
ADD --22"--

Column 3, Line 66:
DELETE "22"
ADD --22"--

Column 5, Line 19:
DELETE "infection"
ADD --injection--

Column 6, Line 7:
DELETE "a"
ADD --at a--

Signed and Sealed this

Seventh Day of December, 2010

David J. Kappos
*Director of the United States Patent and Trademark Office*